US00PP37802P2

(12) United States Plant Patent
Arts

(10) Patent No.: US PP37,802 P2
(45) Date of Patent: Oct. 20, 2026

(54) ***HYDRANGEA* PLANT NAMED 'HP224906'**

(50) Latin Name: *Hydrangea paniculata*
Varietal Denomination: HP224906

(71) Applicant: HYDRANGEA BREEDERS ASSOCIATION B.V., De Kwakel (NL)

(72) Inventor: Niels Arts, Aalsmeer (NL)

(73) Assignee: HYDRANGEA BREEDERS ASSOCIATION B.V., De Kwakel (NL)

( * ) Notice: Subject to any disclaimer, the term of this patent is extended or adjusted under 35 U.S.C. 154(b) by 0 days.

(21) Appl. No.: 19/570,139

(22) Filed: Mar. 17, 2026

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Hydrangea* plant named 'HP224906', characterized by its compact, upright to outwardly spreading and rounded to conical plant habit; vigorous growth habit and rapid growth rate; freely branching habit with thick and sturdy stems; freely and uniformly flowering habit; large broadly pyramidal mophead type inflorescences with numerous yellowish green-colored sterile flowers; and good garden performance.

2 Drawing Sheets

Figure 1:
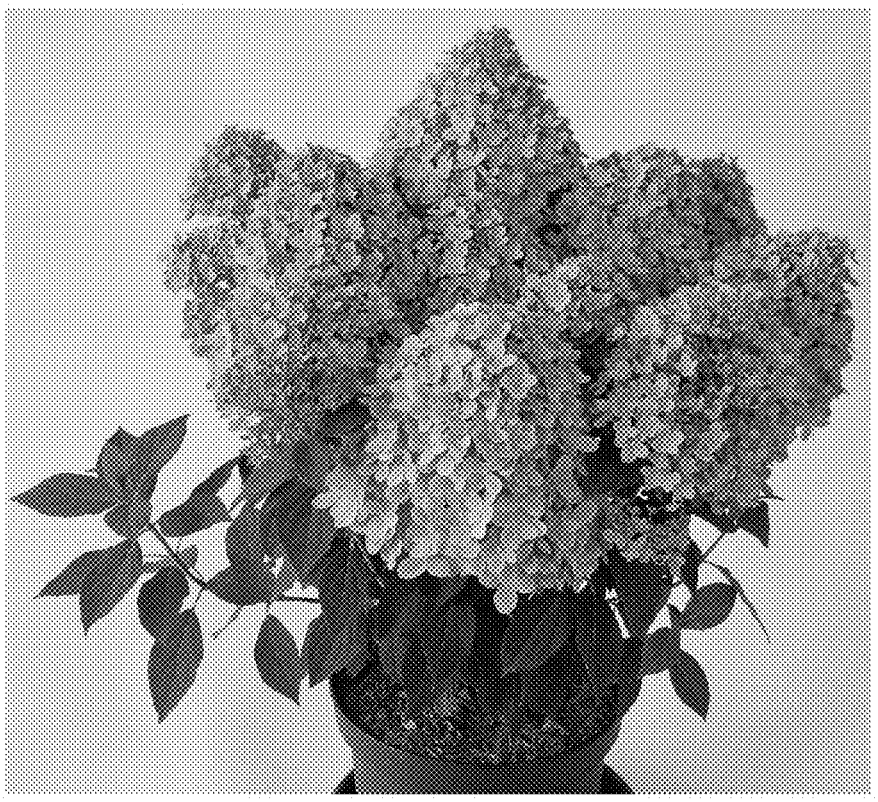

Botanical designation: *Hydrangea paniculata.*
Cultivar denomination: 'HP224906'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, *Hydrangea* Breeders Association B.V. of De Kwakel, The Netherlands on May 13, 2025, application number 2025/1007, and published on Aug. 15, 2025. Foreign priority is not claimed to this application.

BACKGROUND OF THE INVENTION

The present invention relates to a new and distinct cultivar of *Hydrangea* plant, botanically known as *Hydrangea paniculata*, commercially referred to as a Panicle *Hydrangea* and hereinafter referred to by the name 'HP224906'.

The new *Hydrangea* plant is a product of a planned breeding program conducted by the Inventor in De Kwakel, The Netherlands and Lengerich, Germany. The objective of the breeding program was to create new compact and early-flowering *Hydrangea* plants with sturdy stems, large inflorescences with numerous showy sterile flowers and good garden performance.

The new *Hydrangea* plant originated from a cross-pollination made by the Inventor during the summer of 2016 in De Kwakel, The Netherlands, of *Hydrangea paniculata* 'HP217901', disclosed in U.S. Plant Pat. No. 30,307, as the female, or seed, parent with a proprietary breeding selection of *Hydrangea paniculata* identified as code number 11-0417-007, not patented, as the male, or pollen, parent. The new *Hydrangea* plant was discovered and selected by the Inventor as a single flowering plant from within the progeny of the stated cross-pollination in a controlled greenhouse environment in Lengerich, Germany during the spring of 2018.

Asexual reproduction of the new *Hydrangea* plant by vegetative tip cuttings in a controlled environment in De Kwakel, The Netherlands since the summer of 2018 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HP224906'. These characteristics in combination distinguish 'HP224906' as a new and distinct *Hydrangea* plant:

1. Compact, upright to outwardly spreading and rounded to conical plant habit.
2. Vigorous growth habit and rapid growth rate.
3. Freely branching habit with thick and sturdy stems.
4. Freely and uniformly flowering habit.
5. Large broadly pyramidal mophead type inflorescences with numerous yellowish green-colored sterile flowers.
6. Good garden performance.

Plants of the new *Hydrangea* can be compared to plants of the female parent, 'HP217901'. Plants of the new *Hydrangea* differ primarily from plants of 'HP217901' in flowering habit as inflorescences of plants of the new *Hydrangea* have more sterile flowers than inflorescences of plants of 'HP217901'.

Plants of the new *Hydrangea* can be compared to plants of the male parent selection. Plants of the new *Hydrangea* differ primarily from plants of the male parent selection in plant habit as plants of the new *Hydrangea* are more compact than plants of the male parent selection. In addition, inflorescences of plants of the new *Hydrangea* have more sterile flowers than inflorescences of plants of the male parent selection.

Plants of the new *Hydrangea* can be compared to plants of the *Hydrangea paniculata* 'HP217902', disclosed in U.S. Plant Pat. No. 30,332. In side-by-side comparisons, plants of the new *Hydrangea* differ primarily from plants of 'HP217902' in the following characteristics:

1. Plants of the new *Hydrangea* are more compact than plants of 'HP217902'.
2. Plants of the new *Hydrangea* are more freely branching than plants of 'HP217902'.
3. Plants of the new *Hydrangea* have smaller leaves than plants of 'HP217902'.
4. Plants of the new *Hydrangea* have shorter inflorescences than plants of 'HP217902'.
5. Inflorescences of plants of the new *Hydrangea* have larger sterile flowers than inflorescences of plants of 'HP217902'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HP224906' grown in a container.

Figure 2:
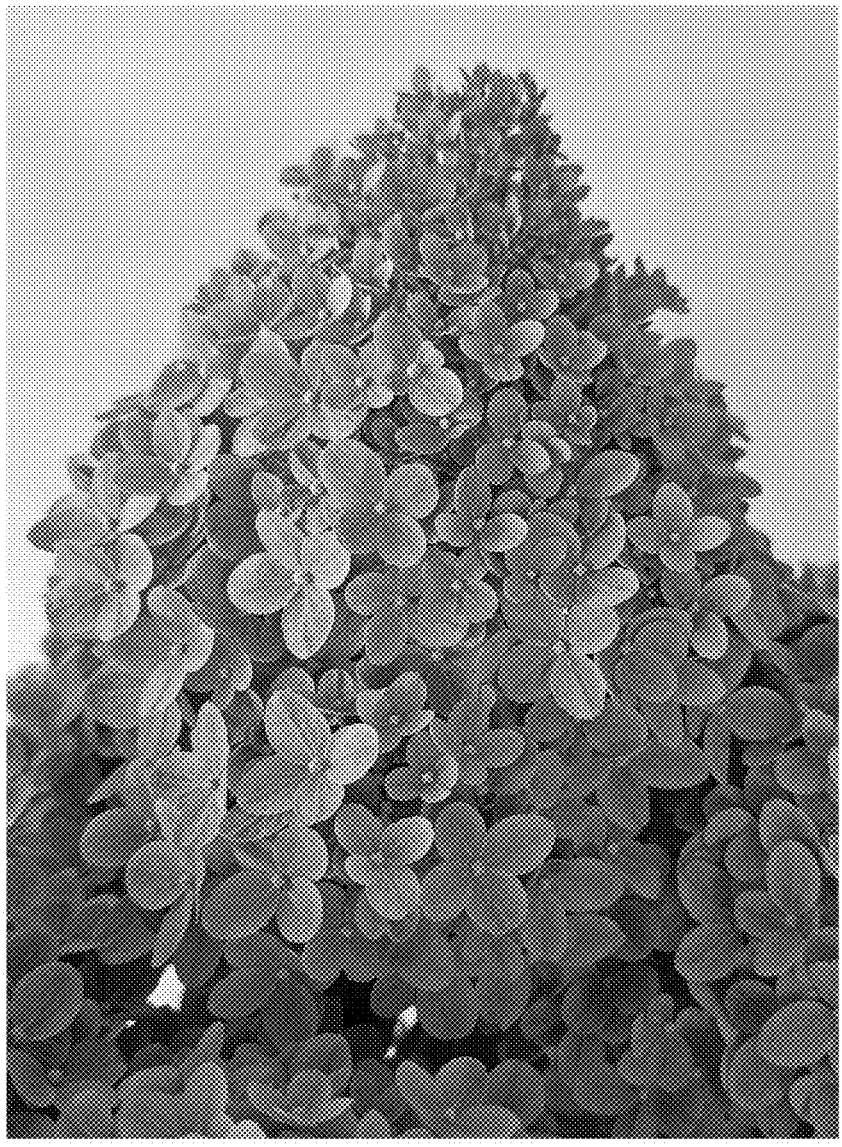

The photograph on the second sheet (FIG. 2) is a close up view of a typical inflorescence of 'HP224906'.

DETAILED BOTANICAL DESCRIPTION

Plants used in the aforementioned photographs and in the following description were grown during the summer in 17-cm containers in an outdoor nursery in Lengerich, Germany and under cultural practices typical of commercial Panicle *Hydrangea* production. During the production of the plants, day and night temperatures averaged 15° C. Plants of the new *Hydrangea* were 17 months old when the photographs and description were taken. In the following description, color references are made to The Royal Horticultural Society Colour Chart, 2015 Edition, except where general terms of ordinary dictionary significance are used.

Botanical description: *Hydrangea paniculata* 'HP224906'.

Parentage:

*Female, or seed, parent.*—*Hydrangea paniculata* 'HP217901', disclosed in U.S. Plant Pat. No. 30,307.

*Male, or pollen, parent.*—Proprietary breeding selection of *Hydrangea paniculata* identified as code number 11-0417-007, not patented.

Propagation:

*Type cutting.*—By vegetative tip cuttings.

*Time to initiate roots, summer.*—About two weeks at temperatures about 23° C.

*Time to initiate roots, winter.*—About 18 days at temperatures about 18° C.

*Time to produce a rooted young plant, summer.*—About four weeks at temperatures about 23° C.

*Time to produce a rooted young plant, winter.*—About five weeks at temperatures about 18° C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Compact, upright to outwardly spreading and rounded plant habit; thick and sturdy stems; vigorous growth habit and rapid growth rate.

*Plant height.*—About 40 cm.

*Plant diameter or area of spread.*—About 40 cm to 50 cm.

Lateral branch description:

*Branching habit.*—Freely branching habit; when pinched, about 16 lateral branches develop per plant.

*Length, stem axis to base of inflorescence.*—About 20 cm to 30 cm.

*Diameter.*—About 5 mm.

*Internode length.*—About 2 cm to 4 cm.

*Texture.*—Smooth, glabrous; fully developed, woody.

*Aspect.*—Mostly upright.

*Strength.*—Sturdy.

*Color.*—Close to 146C; when woody, close to 199B; lenticels, close to 165C.

Leaf description:

*Arrangement.*—Opposite, simple.

*Length.*—About 5 cm to 6 cm.

*Width.*—About 3 cm.

*Shape.*—Ovate.

*Apex.*—Acute.

*Base.*—Obtuse.

*Margin.*—Serrulate.

*Texture, upper surface.*—Rugose, prominent venation; pubescent.

*Texture, lower surface.*—Rugose, prominent venation; glabrous.

*Venation pattern.*—Pinnate.

*Color.*—Developing leaves, upper and lower surfaces: Close to 144A. Fully developed leaves, upper surface: Close to 137B; venation, close to 144A. Fully developed leaves, lower surface: Close to 138B; venation, close to 144C.

*Petioles.*—Length: About 1 cm. Diameter: About 2 mm. Texture, upper and lower surfaces: Smooth, glabrous. Color, upper surface: Close to 144A. Color, lower surface: Close to 144C.

Flower description:

*Flower type and habit.*—Small and inconspicuous fertile flowers and showy sterile flowers arranged on terminal panicles; fertile and sterile flowers round in shape; panicles broadly pyramidal in overall shape; fertile and sterile flowers face upright to outwardly depending on their position in the inflorescence.

*Fragrance.*—None detected.

*Natural flowering season.*—Plants begin flowering about 15 weeks after cold treatment; flowering begins in the early summer and is continuous throughout the summer in Northern Europe.

*Flower longevity*.—Fertile flowers last about one month on the plant, fertile flowers not persistent; sterile flowers last about three months on the plant, sterile flowers persistent.

*Quantity of flowers*.—Freely flowering habit; about 100 fertile flowers develop per panicle and about 300 to 500 sterile flowers develop per panicle.

*Panicle height*.—About 12 cm to 15 cm.

*Panicle diameter*.—About 15 cm to 20 cm.

*Fertile flower buds*.—Length: About 2 mm. Diameter: About 2 mm. Shape: Rounded. Color: Close to 145C.

*Sterile flower buds*.—Length: About 2 mm. Diameter: About 2 mm. Shape: Rounded. Color: Close to 145A.

*Fertile flower diameter*.—About 2 mm.

*Fertile flower depth* (*height*).—About 1 mm.

*Sterile flower diameter*.—About 3 cm.

*Sterile flower depth* (*height*).—About 5 mm.

*Petals, fertile flowers*.—Quantity and arrangement: About five in a single whorl. Length: About 2 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 145C. Fully opened, upper and lower surfaces: Close to 145D; color does not change with subsequent development.

*Petals, sterile flowers*.—Quantity and arrangement: About four in a single whorl. Length: About 2 mm. Width: About 1 mm. Shape: Ovate. Apex: Acute. Base: Cuneate. Margin: Entire. Texture, upper and lower surfaces: Smooth, glabrous. Color: When opening, upper and lower surfaces: Close to 145D. Fully opened, upper and lower surfaces: Close to 157B; color does not change with subsequent development.

*Sepals, fertile flowers*.—Quantity and arrangement: About five in a single whorl. Length: About 1 mm. Width: About 1 mm. Shape: Ovate. Apex: Acute. Base: Fused. Margin: Entire. Texture, upper and lower surfaces: Smooth, glabrous. Color: When opening, upper and lower surfaces: Close to 145A. Fully opened, upper and lower surfaces: Close to 145A; color does not change with subsequent development.

*Sepals, sterile flowers*.—Quantity and arrangement: About four in a single whorl. Length: About 1.5 cm. Width: About 1 cm. Shape: Elliptic. Apex: Obtuse. Base: Obtuse. Margin: Entire. Texture, upper and lower surfaces: Smooth, glabrous. Color: When opening, upper and lower surfaces: Close to 145B. Fully opened, upper and lower surfaces: Close to 145A; in the autumn, color may become closer to 63A and 185D with subsequent development.

*Pedicels, fertile flowers*.—Length: About 2 mm. Diameter: About 1 mm. Strength: Sturdy. Aspect: Mostly upright. Texture: Smooth, glabrous. Color: Close to 145B.

*Pedicels, sterile flowers*.—Length: About 1.5 cm to 2 cm. Diameter: About 1 mm to 2 mm. Strength: Sturdy. Aspect: About 80° to 90° from branch axis. Texture: Smooth, glabrous. Color: Close to 145C.

*Reproductive organs, fertile flowers*.—Stamens: Quantity per flower: About nine to ten. Filament length: About 3 mm. Filament color: Close to 157D. Anther length: About 1 mm. Anther shape: Round. Anther color: Close to 157D. Pollen amount: Moderate. Pollen color: Close to 84D. Pistils: Pistil quantity per flower: One. Pistil length: About 0.5 mm to 1 mm. Stigma shape: Two to three-lobed. Stigma color: Close to 146C. Style length: About 0.5 mm. Style color: Close to 146C. Ovary color: Close to 157C.

*Reproductive organs, sterile flowers*.—Stamens: Quantity per flower: About nine to ten. Filament length: About 3 mm. Filament color: Close to 157D. Anther length: About 1 mm. Anther shape: Round. Anther color: Close to 157D. Pollen amount: Scarce. Pollen color: Close to 84D. Pistils: To date, pistil development has not been observed on sterile flowers of plants of the new *Hydrangea*.

*Seeds, only produced by fertile flowers*.—Quantity per fertile flower: About 20 to 30. Length: Less than 0.5 mm. Diameter: Less than 0.5 mm. Color: Close to 199A.

Pathogen & pest resistance: To date, plants of the new *Hydrangea* grown under commercial production conditions have not been observed to be resistant to pathogens and pests common to *Hydrangea* plants.

Garden performance: Plants of the new *Hydrangea* have been shown to have good garden performance and to be tolerant to wind, rain and temperatures ranging from about −38° C. to about 38° C.

It is claimed:

1. A new and distinct *Hydrangea* plant named 'HP224906' as herein illustrated and described.

* * * * *